United States Patent [19]  [11] 3,965,155
Smith et al.  [45] *June 22, 1976

[54] PROCESS FOR PREPARING VINYL ESTERS OF CARBOXYLIC ACIDS

[75] Inventors: William E. Smith, Schenectady; R. John Gerhart, Averill Park, both of N.Y.

[73] Assignee: General Electric Company, Pittsfield, Mass.

[ * ] Notice: The portion of the term of this patent subsequent to June 22, 1993, has been disclaimed.

[22] Filed: Feb. 4, 1974

[21] Appl. No.: 439,443

[52] U.S. Cl. ......................... 260/491; 260/604 AC; 260/410.9 N
[51] Int. Cl.² ..................................... C07C 67/00
[58] Field of Search ................ 260/497 A, 410.9 N, 260/491

[56] References Cited
UNITED STATES PATENTS

| | | |
|---|---|---|
| 3,277,158 | 10/1966 | Schaeffer ........................ 260/497 A |
| 3,306,930 | 2/1967 | Copelin ........................... 260/497 A |
| 3,328,439 | 6/1967 | Hamilton ........................... 260/491 |
| 3,346,624 | 10/1967 | Schaeffer et al. ................ 260/497 A |
| 3,444,189 | 5/1969 | Oliver ............................. 260/497 A |
| 3,450,748 | 6/1969 | Schaeffer ........................ 260/497 A |

FOREIGN PATENTS OR APPLICATIONS

| | | | |
|---|---|---|---|
| 1,443,882 | 10/1968 | Germany | ..................... 260/497 A |

OTHER PUBLICATIONS

Somanos, *Jour. of Catalysis,* 23, 19–30, (1971).

*Primary Examiner*—Lorraine A. Weinberger
*Assistant Examiner*—Michael Shippen
*Attorney, Agent, or Firm*—Donald M. Papuga; William F. Mufatti

[57] ABSTRACT

A process for preparing vinyl esters of carboxylic acids which comprises reacting ethylene, a lower alkyl carboxylate ester, water and oxygen in the presence of a catalyst system comprising an oxidation catalyst and an acidic co-catalyst.

6 Claims, No Drawings

PROCESS FOR PREPARING VINYL ESTERS OF CARBOXYLIC ACIDS

This invention relates to a process for preparing vinyl esters of carboxylic acids which comprises reacting ethylene, a lower alkyl carboxylate ester, water and oxygen in the presence of a catalyst system comprising an oxidation catalyst and an acidic co-catalyst.

BACKGROUND OF THE INVENTION

Vinyl esters of carboxylic acids have been prepared by a number of different methods. A useful method of preparing vinyl acetate, for example, is by contacting ethylene with a palladium catalyst in the presence of oxygen and acetic acid. This is illustrated by U.S. Pat. No. 3,658,888 for example. Vinyl acetate is useful as an intermediate for the manufacture of polymers and other valuable materials.

DESCRIPTION OF THE INVENTION

The primary object of the present invention concerns a process for preparing vinyl esters of carboxylic acids which comprises reacting ethylene, a lower alkyl carboxylate ester, water and oxygen in the presence of a catalyst system comprising an oxidation catalyst and an acidic co-catalyst. Preferably, the lower alkyl carboxylate is methyl acetate.

The process may be illustrated, taking the formation of vinyl acetate as an example, by equation 1:

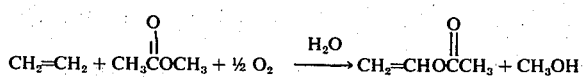  (1)

This transformation is actually the net of the processes represented in equations 2 and 3:

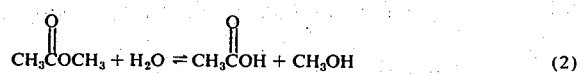  (2)

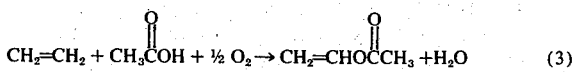  (3)

The hydrolysis depicted in equation 2 is promoted by the acidic co-catalyst, providing substantial amounts of the acetic acid needed for the oxidation process represented by equation 3.

The lower alkyl carboxylate esters which may be employed in the instant invention are illustrated by the following structure:

wherein $R_1$ and $R_2$ can contain from one to about eight carbon atoms. The preferred lower alkyl carboxylate ester is methyl acetate.

The catalyst system of the instant invention comprises an oxidation catalyst and an acidic co-catalyst. The oxidation component of the catalyst may be selected from the group consisting of a Group VIII noble metal, or its salts, or its oxides, or mixtures thereof. Specific examples of such catalysts include metals such as palladium, ruthenium, rhodium, platinum, osmium, and iridium as well as oxides and salts such as palladous propionate, palladous benzoate, palladous chloride, palladous bromide, palladous oxide, etc., ruthenium acetate, etc., rhodium acetate, etc., platinous benzoate, platinum dichloride, platinum oxide, etc., iridium chloride, etc., and the like and mixtures thereof.

The preferred oxidation catalyst is a mixture of the Group VIII noble metal and its salt. A more preferred oxidation catalyst is a mixture of palladium and palladous acetate.

The acidic co-catalyst may be an acidic support material such as alumina or silica or the like or may be a more active substance present in smaller amounts.

A promoter may be added to the catalyst system which influences activity and selectivity. Among the preferred promoters are the alkali metal and alkaline earth metal carboxylates, the transition metals, their salts, gold or copper.

The catalyst may be prepared in a number of different ways. For example, a support such as aluminum oxide is impregnated with a palladium acetyl acetonate solution in benzene and dried. The resulting material is then impregnated with a solution of potassium acetate in water and dried. The catalyst is then treated with ethylene, which reduces the palladium to the metallic state. The catalyst thus obtained contains palladium metal and potassium acetate in about 1:10 parts.

Varying amounts of the catalyst can be used within the scope of this invention. Amounts as low as about .1% based on weight of support have been found to be effective.

Water serves the dual function of hydrolyzing the lower alkyl carboxylate and moderating the oxidation reaction.

The working temperature is in the range of from about 100°C. to about 200°C. For optimum production of the vinyl ester, the temperature is in the range from about 125°C. to about 160°C. At higher temperatures, significant quantities of acetaldehyde are produced. The working pressure is in the range from about atmospheric to about 150 psi. Somewhat higher or lower temperatures and pressures may, however, be used within the scope of the invention.

The oxygen in the instant process may be used in pure elementary form or in admixture with inert gases, for example, in the form of air. However, it is preferred to work with concentrated oxygen.

The ethylene in the instant process may be used in pure form or in admixture with inert compounds, for example, saturated hydrocarbons.

In carrying out the invention, ethylene and methyl acetate, for example, are passed through a bed of the catalyst in a tube reactor with water and oxygen at temperatures of from about 100°C. to about 160°C. at about 80 psi. Upon leaving the reaction zone, the products are condensed and a two phase mixture forms. The upper phase is a mixture of, in this case, methyl acetate, vinyl acetate and methanol. The lower phase is principally water and methanol, with a small amount of vinyl acetate. Traces of acetaldehyde are present in both phases. Direct distillation of the mixture affords the methanol and methyl acetate for recycle, leaving a two phase mixture of vinyl acetate and water. The vinyl acetate phase is decanted in a form suitable for further use.

On increasing the temperature and the activity of the acidic component of the catalyst, significant quantities of acetaldehyde are formed.

The ester starting material (for example methyl acetate) may be supplemented with the carboxylic acid (for example acetic acid) itself, with equally satisfactory results.

As is known in the art (Encyclopedia of Polymer Science and Technology, Vol. 15, *Vinyl Acetate Polymers*, pp. 577–677, Interscience, New York, 1971), vinyl acetate may be converted directly to poly(vinyl acetate). As is also known in the art (Encyclopedia of Polymer Science and Technology, Vol. 14, *Vinyl Alcohol Polymers*, pp. 149–239, Interscience, New York, 1971), the poly(vinyl acetate) on reaction with methanol is converted to poly(vinyl alcohol), with liberation of the acetate moiety as methyl acetate. The above reference to the Encyclopedia of Polymer Science and Technology are incorporated herein by reference. Thus, with recycle of the methyl acetate, an efficient and economical overall process for producing poly(vinyl alcohol) from ethylene is possible (equations 4–6).

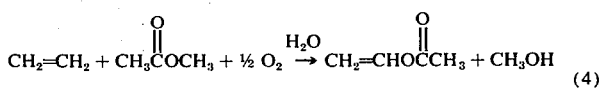

(4)

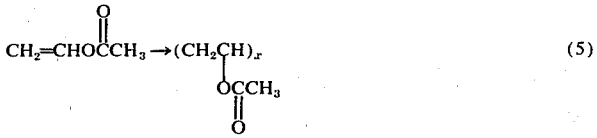

(5)

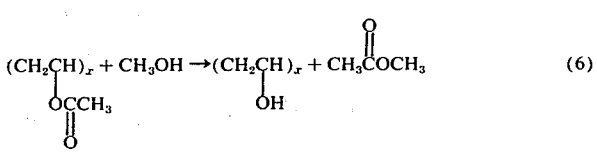

(6)

DESCRIPTION OF THE PREFERRED EMBODIMENT

The following examples are set forth to illustrate more clearly the principle and practice of this invention to those skilled in the art. Unless otherwise specified, where parts or percents are mentioned, they are parts or percents by weight.

EXAMPLE 1

An 8 ft. × 1 in. diameter stainless steel tube is charged with one liter (1000 grams) of catalyst composed of 3/16 in. alumina pellets impregnated with palladium (0.3%) and potassium acetate (3%). The reactor temperature is maintained at 155°C. (circulating oil jacket) while a mixture per hour of 1500 grams of ethylene, 740 grams of methyl acetate, 900 grams of water and 170 grams of oxygen is passed through under pressure of about 80 psi. The output per hour is a mixture (two liquid phases) of about 215 grams of vinyl acetate, 66 grams of acetaldehyde, 77 grams of methanol, 510 grams of unconverted methyl acetate (69% recovery), a trace of acetic acid, and the excess water and ethylene (these results determined by quantitative glpc analysis).

EXAMPLE 2

The tube, catalyst and general procedure described in Example 1 are employed, the reagent quantities differing only in the amount of water, which is doubled to 1800 grams. Analysis of the effluent in this case shows the collection per hour of 268 grams of vinyl acetate, 71 grams of acetaldehyde, 131 grams of methanol, 423 grams of methyl acetate (57% recovery), a very small amount of acetic acid, and the excess water and ethylene.

EXAMPLE 3

The tube, catalyst and procedure described in Example 1 are employed, with substitution of 910 grams of the methyl acetate-methanol azeotrope (composed of 740 grams of methyl acetate and 170 grams of methanol) for the pure methyl acetate. Analysis indicates the presence of the effluent of (per hour) 140 grams of vinyl acetate, 84 grams of acetaldehyde, 205 grams of methanol and 595 grams of unconverted methyl acetate (80% recovery).

EXAMPLE 4

The tube, catalyst and general procedure described in the above examples are employed, with use of 910 grams of the methyl acetate-methanol azeotrope described in Example 3 and 1800 grams of water. Analysis indicates the presence in the effluent of (per hour) 218 grams of vinyl acetate, 90 grams of acetaldehyde, 258 grams of methanol and 527 grams of unconverted methyl acetate (71% recovery).

Obviously, other modifications and variations of the present invention are possible in the light of the above teachings. It is therefore to be understood that changes may be made in the particular embodiments of the invention described which are within the full intended scope of the invention as defined by the appended claims.

What is claimed is:

1. A vapor phase process for preparing vinyl esters of carboxylic acids which comprises reacting ethylene, a lower alkyl carboxylate ester, water and oxygen in the presence of a catalyst system comprising an oxidation catalyst selected from the group consisting of a Group VIII noble metal or its salts, or its oxides or mixtures thereof and an acidic co-catalyst which is an acidic support material at a temperature of from about 100°C to about 200°C.

2. The process of claim 1 wherein the acidic support is alumina or silica.

3. The process of claim 1 wherein a lower alkyl carboxylic acid is used in combination with the lower alkyl carboxylate ester.

4. A vapor phase process of preparing vinyl acetate which comprises reacting ethylene, methyl acetate, water and oxygen in the presence of a catalyst system comprising a Group VIII noble metal, or its salts, or its oxides, or mixtures thereof and an acidic co-catalyst which is an acidic support material at a temperature of from about 100°C to about 160°C.

5. The process of claim 4 wherein the acidic support is alumina or silica.

6. The process of claim 4 wherein acetic acid is used in combination with methyl acetate.

* * * * *